(12) United States Patent
Hess et al.

(10) Patent No.: US 7,655,416 B2
(45) Date of Patent: *Feb. 2, 2010

(54) DIAGNOSING RISK OF CARDIOVASCULAR COMPLICATIONS USING NATIURETIC PEPTIDES

(75) Inventors: Georg Hess, Mainz (DE); Andrea Horsch, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 70 days.

This patent is subject to a terminal disclaimer.

(21) Appl. No.: 11/610,045

(22) Filed: Dec. 13, 2006

(65) Prior Publication Data

US 2007/0190573 A1    Aug. 16, 2007

Related U.S. Application Data

(63) Continuation of application No. PCT/EP2005/006359, filed on Jun. 14, 2005.

(30) Foreign Application Priority Data

Jun. 15, 2004  (EP) .................................. 04013954

(51) Int. Cl.
*G01N 33/53* (2006.01)
(52) U.S. Cl. ........................ 435/7.1; 435/7.2; 435/91.2; 435/805; 435/810; 436/501; 436/514; 436/518
(58) Field of Classification Search .................. 435/7.1, 435/91.2, 805, 810; 436/501, 514, 518
See application file for complete search history.

(56) References Cited

U.S. PATENT DOCUMENTS 5,744,305 A    4/1998    Fodor et al.

FOREIGN PATENT DOCUMENTS

| WO | 02/083913 A1 | 10/2002 |
| WO | 02/089657 A3 | 11/2002 |
| WO | WO 02/083913 | * 10/2008 |

OTHER PUBLICATIONS

Neri et al., Int. J. Clin. Pham Re. 1991; 11:75-81.*
Okumura et al., Acta Haematol 2000; 104:158-163.*
Nousiainen et al., Eur. J. Haematol. 1999; 62:135-141.*
Von Hoff et al., Annals of Internal Medicine. 1979; 81:710-77.*
Nousiainen et al., Journal of Internal Medicine. 2002; 251:228-234.*
Ala-Kopsala, M, et al., "Molecular Heterogenity Has a Major Impact on the Measurement of Circulating N-Terminal Fragments of A- and B- Type Natriuretic Peptides," Clinical Chemstry 50:9, 1576-1588 (2004).
Barbaro, G. et al., "Cardiovascular Manifestations of HIV Infection," Circulation, vol. 166 (1996) 1420-1425.
Bonow, R. et al., "New Insights Into the Cardiac Natriuretic Peptides," Circulation 93:11, Jun. 1, 1996, 1946-1950.
Meinardi, M.T. et al., "Prospective Evaluation of Early Cardiac Damage Induced by Epirubicin-Containing Adjuvant Chemotherapy and Locoregional Radiotherapy in Breast Cancer Patients," Journal of Clinical Oncology 19:10 (May 15, 2001) 2746-2753.
Mohideen, M. R. et al., "Brain Natriuretic Peptide is more than a Marker," Ceylon Medical Journal 47:3, Sep. 2002, 81-82.
Mueller, T. et al., "Comparrison of the Biomedica NT-proBNP Enzyme Immunoassay and the Roche NT-proBNP Chemiluminescence Immunoassay: Implications for the Prediction of Symptomatic and Asymptomatic Structural Heart Disease," Clinical Chemistry 49, No. 6, 2003, 976-979.
Nielsen, L et al., "N-terminal pro-brain natriuretic peptide for discriminating between cardiac and non-cardiac dyspnoea," The European Journal of Heart Failure 6 (2004) 63-70.
Nolan, J. et al., "Suspension array technology: evolution of the flat-array paradigm," Trends in Biotechnology 20:1 (Jan. 2002) 9-12.
Okumura, H. et al., "Brain Natriuretic Peptide Is a Predictor of Anthracycline-Induced Cardiotoxicity," Acta Haematol 2000; 104:158-163.
Sundsfjord, J. et al., "Identification and Plasma Concentrations of the N-Terminal Fragment of Proatrial Natriuretic Factor in Man," Journal of Endocrinology and Metabolism 66:3, 1988, 605-610.
Suzuki, T. et al., "Elevated B-Type Natriuretic Peptide Levels After Anthracycline Administration," American Heart Journal 136:2, (1998) 362-363.
Tsekoura, D. et al., "Brain Natriuretic Peptide," Hellenic J. Cardiol 44:266-270 (2003).

* cited by examiner

*Primary Examiner*—Bao-Thuy L Nguyen
(74) *Attorney, Agent, or Firm*—Marilyn Amick; Roche Diagnositcs Operations, Inc.

(57) ABSTRACT

The present invention relates to the use of cardiac hormones, particularly natriuretic peptides, for diagnosing the risk of suffering from a cardiovascular complication, particularly heart disease or acute coronary syndrome, as a consequence of cardiotoxic medication, in particular chemotherapeutics, including anthracyclines. In particular, the invention relates to a method for diagnosing the risk of a patient who is going to receive cardiotoxic medication of suffering from a cardiovascular complication as a consequence of the cardiotoxic medication, comprising the steps of (a) taking a body fluid or tissue sample, and (b) measuring, preferably in vitro, the level of a cardiac hormone. Preferred cardiac hormones in the context of the present invention are ANP, NT-proANP, BNP, and NT-proBNP.

11 Claims, 4 Drawing Sheets

DIAGNOSING RISK OF CARDIOVASCULAR COMPLICATIONS USING NATIURETIC PEPTIDES

RELATED APPLICATIONS

This application is a continuation of PCT PCT/EP2005/006359 filed Jun. 14, 2005 and claims priority to EP 04013954.5 filed Jun. 15, 2004.

FIELD OF THE INVENTION

The present invention relates to diagnosing of the risk of suffering from a cardiovascular complication as a consequence of cardiotoxic medication.

BACKGROUND OF THE INVENTION

An aim of modern medicine is to provide personalized or individualized treatment regimens. Those are treatment regimens which take into account a patient's individual needs or risks. A particularly important risk is the presence of a cardiovascular complication, particularly an unrecognized cardiovascular complication.

Cardiovascular complications, particularly heart diseases, are the leading cause of morbidity and mortality in the Western hemisphere. It is known that cardiovascular complications can result from certain medications, e.g. anthracycline treatment, that show cardiotoxic effects. In many cases, the risk associated with cardiotoxic medication is dose-limiting.

The use of natriuretic peptides as molecular or biochemical markers is known as such. In WO 02/089657, it has been suggested to measure brain natriuretic peptide (BNP) to diagnose myocardial infarction. In WO 02/083913 it has been suggested to use BNP to predict near-term morbidity or mortality in patients with congestive heart failure, myocardial infarction, ST-elevated myocardial infarction, or non-ST-elevated acute coronary syndromes.

Suzuki et al. have investigated whether anthracyclines can influence the plasma concentration of BNP (Suzuki, T., et al. (1998). Elevated B-type natriuretic peptide levels after anthracycline administration. American Heart Journal, vol. 136(2), p. 362-363.). The study suggests the possible use of BNP levels to assess the cardiac state after anthracycline administration. According to their interpretation, BNP levels most likely reflect cardiac tolerance to the cardiotoxic agent.

Okumura et al. investigated whether BNP can be used as a predictor of cardiotoxicity in patients with acute leukaemia treated with a daunorubicin-containing regimen (Okumura, H., et al. (2000). Brain natriuretic peptide is a predictor of anthracycline-induced cardiotoxicity. Acta Haematologica, vol. 104, p. 158-163). The authors conclude that their preliminary results suggest that BNP may be useful as an early and sensitive indicator of anthracycline induced cardiotoxicity.

However, the value of BNP as a diagnostic marker in the context of cardiotoxicity is still subject to debate. A recent review questions whether BNP can be used to monitor drug-related cardiotoxicity (Mohideen, M. R. (2002), Brain natriuretic peptide is more than a marker. Ceylon Medical Journal, vol. 47(3), p. 81-82). Another recent review, published after the review mentioned beforehand, comes to the conclusion that there are "no encouraging data" concerning the early diagnosis of left ventricular dysfunction using BNP for diagnosing cardiotoxicity caused by anthracyclines (Tsekoura, D. K., et al. (2003). Brain natriuretic peptide. Hellenic Journal of Cardiology, vol. 44, p. 266-270).

The role of NT-proBNP for diagnosis of cardiotoxicity mediated by anthracyclines has not been subject to investigation.

Furthermore, the prior art relates only to a potential use of BNP for monitoring cardiotoxicity, i.e. cardiotoxicity caused by a drug after treatment has already commenced.

However, it would be preferable if risk patients could be identified even before they receive cardiotoxic medication. It is important to realize that cardiovascular complications can remain asymptomatic for long periods of time. Therefore, reliable diagnosis of the presence of a cardiovascular complication is more difficult and error-prone than generally believed (Svendstrup Nielsen, L., et al. (2003). N-terminal pro-brain natriuretic peptide for discriminating between cardiac and non-cardiac dyspnoea. The European Journal of Heart Failure).

Currently, only patients with a known history of heart disease or hypertension receive closer monitoring in case of a treatment with cardiotoxic medication. In particular, general practitioners and non-cardiologists have no simple means to identify a previously unrecognized cardiovascular problem.

Therefore, there is a need to for a method or means to identify risk patients before they receive cardiotoxic medication. Particularly, there is a need to provide a suitable diagnostic means. Particularly, there is a need for a diagnostic means that allows to identify risk patients that have no history of a cardiovascular complication. In particular, the diagnostic means should be simple, fast, reliable and suited for use by general practitioners and non-cardiologists. Accordingly, it is the object of the present invention to provide such means and methods.

SUMMARY OF THE INVENTION

The object of the invention is attained by a method for diagnosing the risk of a patient of suffering from a cardiovascular complication as a consequence of cardiotoxic medication, comprising the steps of
  a) measuring, preferably in vitro, the patient's level of a cardiac hormone, particularly a natriuretic peptide,
  b) diagnosing the risk of the patient by comparing the measured level to known levels associated with different grades of risk in a patient.

The method may also comprise the step of taking a body fluid or tissue sample of the patient.

The object of the invention is also attained by use of a diagnostic means for measuring, preferably in vitro, a patient's level of a cardiac hormone, particularly a natriuretic peptide, for diagnosing the patient's risk of suffering from a cardiovascular complication as a consequence of cardiotoxic medication. Preferably the level is determined in a body fluid or tissue sample of the patient.

The present invention provides simple and inexpensive methods and means to screen patients, who are receiving or are about to receive cardiotoxic medication, for their risk to develop a cardiovascular complication as a consequence of said cardiotoxic medication. The present invention also provides levels of cardiac hormones indicating the existence or severity of a cardiovascular complication in patients with or without obvious symptoms of a cardiovascular complication.

The present invention also allows adapting the dose of a drug to the risk of a patient. For many cardiotoxic drugs, e.g. anthracyclines, it is preferable to start with the highest possible dosage. However, adapting the dosage of a drug can be difficult or even impossible once treatment has commenced. Therefore, to minimize the risk of cardiovascular complication, frequently a dosage of the cardiotoxic drug is chosen that is too small to show the optimal therapeutic benefit. As the present invention allows the diagnosis or assessment of the risk before treatment commences, the dose of cardiotoxic medication can be optimized, particularly increased, to maximize the therapeutic benefit in each patient while avoiding cardiovascular complication.

Thus, the present invention allows a careful and informed decision about whether to apply cardiotoxic medication, the dosage thereof, and/or to arrange for suitable accompanying treatment or monitoring.

DETAILED DESCRIPTION OF THE INVENTION

Figure 1:
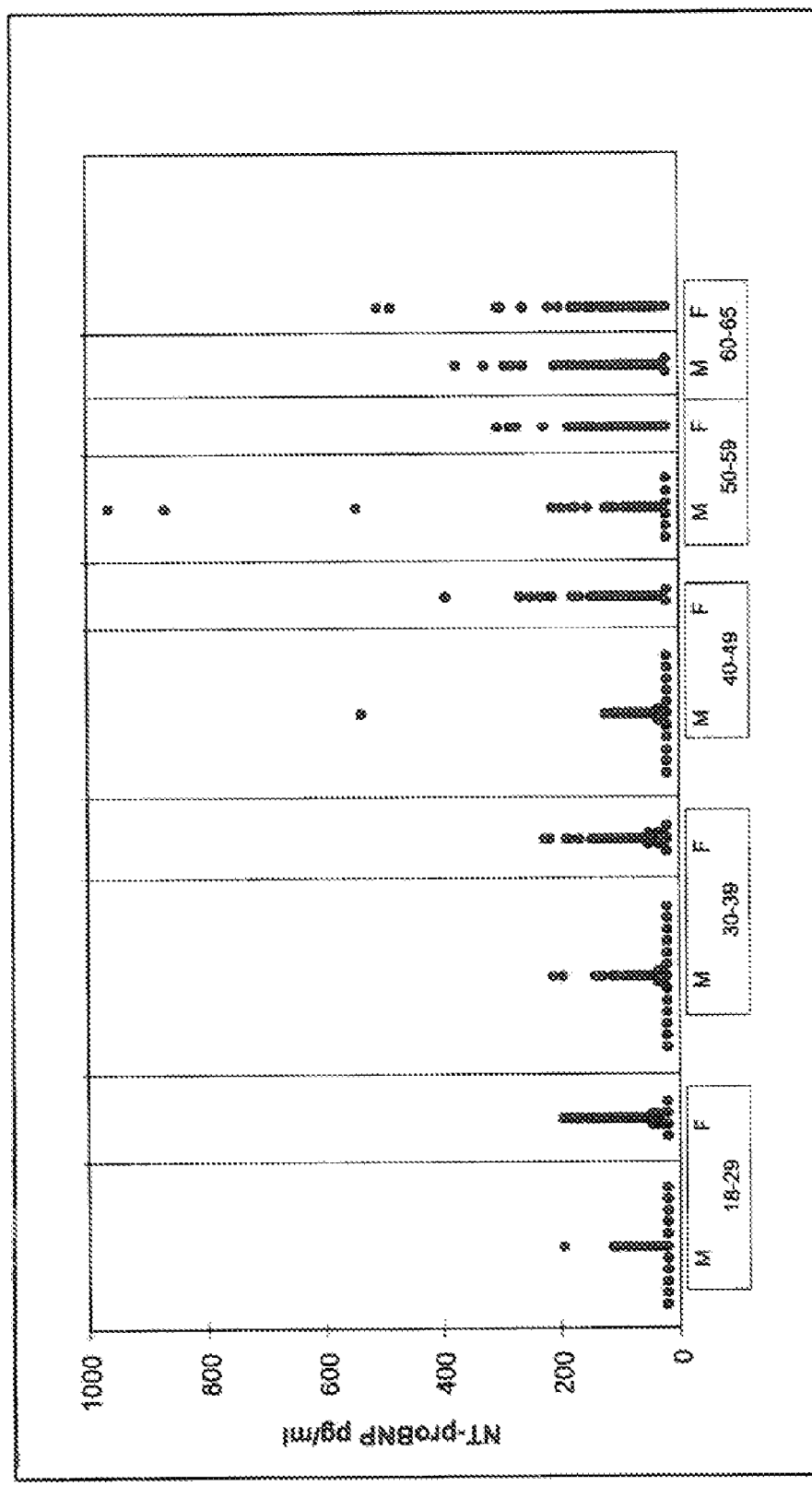
FIG. 1: Frequency distribution of NT-proBNP levels (median) in blood donors (n=2948) at the age of 18-65 years (18-29 years, 30-39 years, 40-49 years, 50-59 years, 60-65 years). M, male; F, female.

The present invention is particularly advantageous to general practitioners, specialized physicians, and specialized wards, departments, or clinics which frequently have no access to extensive cardiological examination by cardiologists. The present invention provides means and methods to such non-cardiologists for simple and reliable screening of patients for those patients who are posed at risk of suffering from a cardiovascular complication as a consequence of cardiotoxic medication.

The invention takes advantage of certain biochemical or molecular markers. The terms "biochemical marker" and "molecular marker" are known to the person skilled in the art. In particular, biochemical or molecular markers are gene expression products which are differentially expressed (i.e. upregulated or downregulated) in the presence or absence of a certain condition, disease, or complication. Usually, a molecular marker is defined as a nucleic acid (such as an mRNA), whereas a biochemical marker is a protein or peptide. The level of a suitable biochemical or molecular marker can indicate the presence or absence of the condition, disease, or complication, and thus allow diagnosis.

The present invention particularly takes advantage of cardiac hormones, more particularly natriuretic peptides, as biochemical markers. Also taking advantage of combinations of any cardiac hormones or natriuretic peptides as biochemical markers is considered in the context of the present invention.

The cardiac hormones according to the present invention comprise natriuretic peptides an urotensin. Particularly, cardiac hormones according to the present invention are natriuretic peptides.

Natriuretic peptides according to the present invention comprise ANP-type and BNP-type peptides and variants thereof (see e.g. Bonow, R. O. (1996). New insights into the cardiac natriuretic peptides. Circulation 93: 1946-1950).

ANP-type peptides comprise pre-proANP, proANP, NT-proANP, and ANP.

BNP-type peptides comprise pre-proBNP, proBNP, NT-proBNP, and BNP.

The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP).

Preferred natriuretic peptides according to the present invention are NT-proANP, ANP, NT-proBNP, BNP, and variants thereof. ANP and BNP are the active hormones and have a shorter half-life than their respective inactive counterparts, NT-proANP and NT-pro BNP. Therefore, depending on the time-course that is of interest, either measurement of the active or the inactive forms can be advantageous. The most preferred natriuretic peptides according to the present invention are NT-proBNP and variants thereof.

The term "variants" in this context relates to peptides substantially similar to said peptides. The term "substantially similar" is well understood by the person skilled in the art. In particular, a variant may be an isoform or allele which shows amino acid exchanges compared to the amino acid sequence of the most prevalent peptide isoform in the human population. Preferably, such a substantially similar peptide has a sequence similarity to the most prevalent isoform of the peptide of at least 80%, preferably at least 85%, more preferably at least 90%, most preferably at least 95%. Substantially similar are also degradation products, e.g. proteolytic degradation products, which are still recognized by the diagnostic means or by ligands directed against the respective full-length peptide. The term "variants" is also meant to relate to splice variants.

The term "variant" also relates to a post-translationally modified peptide such as glycosylated peptide. A "variant" is also a peptide which has been modified after collection of the sample, for example by covalent or non-covalent attachment of a label, particularly a radioactive or fluorescent label, to the peptide.

Examples of particular variants and methods for their measurement are known are known (see e.g. Ala-Kopsala, M., Magga, J., Peuhkurinen, K. et al. (2004): Molecular heterogeneity has a major impact on the measurement of circulating N-terminal fragments of A-type and B-type natriuretic peptides. Clinical Chemistry, vol. 50(9), 1576-1588).

Other embodiments of the invention include the measuring of different markers in combination, simultaneously or non-simultaneously. An example is measuring of NT-proBNP in combination with BNP. Another example is the measuring of a natriuretic hormone, particularly NT-proBNP, in combination with a marker of cardiac necrosis such as Troponin-T, CK-MB, or myoglobin.

Diagnosing according to the present invention includes determining, monitoring, confirmation, subclassification and prediction of the relevant disease, complication, or risk. Determining relates to becoming aware of a disease, complication, or risk. Monitoring relates to keeping track of an already diagnosed disease, or complication, e.g. to analyze the progression of the disease or the influence of a particular treatment on the progression of disease or complication. Confirmation relates to the strengthening or substantiating a diagnosis already performed using other indicators or markers. Subclassification relates to further defining a diagnosis according to different subclasses of the diagnosed disease, e.g. defining according to mild and severe forms of the disease. Prediction relates to prognosing a disease or complication before other symptoms or markers have become evident or have become significantly altered.

Individuals suffering from a cardiovascular disease can be individuals suffering from stable angina pectoris (SAP) and individuals with acute coronary syndromes (ACS). ACS patients can show unstable angina pectoris (UAP) or these individuals have already suffered from a myocardial infarction (MI). MI can be an ST-elevated MI or a non-ST-elevated MI. The occurring of an MI can be followed by a left ventricular dysfunction (LVD). Finally, LVD patients undergo congestive heart failure (CHF) with a mortality rate of roughly 15%.

Cardiovascular diseases have been classified into a functional classification system according to the New York Heart Association (NYHA). Patients of Class I have no obvious symptoms of cardiovascular disease. Physical activity is not limited, and ordinary physical activity does not cause undue fatigue, palpitation, or dyspnea (shortness of breath). Patients of class II have slight limitation of physical activity. They are comfortable at rest, but ordinary physical activity results in fatigue, palpitation, or dyspnea. Patients of class III show a marked limitation of physical activity. They are comfortable at rest, but less than ordinary activity causes fatigue, palpitation, or dyspnea. Patients of class IV are unable to carry out any physical activity without discomfort. They show symptoms of cardiac insufficiency at rest. If any physical activity is undertaken, discomfort is increased.

Accordingly, patients can be divided into individuals showing no clinical symptoms and those with symptoms (e.g. dyspnea).

Another characteristic of cardiovascular diseases can be the "left ventricular ejection fraction" (LVEF) which is also known as "ejection fraction". People with a healthy heart usually have an unimpaired LVEF, which is generally described as above 50%. Most people with a systolic heart disease which is symptomatic generally have an LVEF of 40% or less.

The present invention relates to "cardiovascular complications" developing as a consequence of cardiotoxic medication.

A "cardiovascular complication" according to the present invention relates to any cardiovascular disease or event. In so far as the cardiovascular disease or event causes a secondary complication, e.g. pulmonary congestion or congested lung (which can result e.g. from left ventricular insufficiency), also the secondary complication is understood to be encompassed by the term "cardiovascular complication".

Particularly, "cardiovascular complication" relates to coronary heart disease, SAP, ACS, UAP, MI ST-elevated MI, non-ST-elevated MI, LVD, or CHF.

More particularly, "cardiovascular complication" relates to ACS, UAP, MI, ST-elevated MI, non-ST-elevated MI, LVD, or CHF.

A cardiovascular complication according to the present invention may cause symptoms, particularly symptoms according to NYHA class II-IV, more particularly according to NYHA class III-IV.

A cardiovascular complication may be associated with an LVEF of 40% or less.

A cardiovascular complication may either be "compensated" or "decompensated". Compensated means that the regular oxygen need of the body can still be satisfied, whereas decompensated means that the regular oxygen need of the body is not satisfied anymore.

"Suffering from a cardiovascular complication" according to the present invention also includes deterioration of a pre-existing cardiovascular complication.

The term "patient" according to the present invention relates to a healthy individual, an apparently healthy individual, or, particularly, an individual suffering from a disease. Particularly, the patient is suffering from or treated for AIDS, cancer (e.g. Kaposi's sarcoma, breast cancer, prostate cancer, or leukemia), or a neurological disorder (e.g. multiple sclerosis or depression). Even more particularly, the patient has no known history of cardiovascular complication, and/or no or little (NYHA class I or II) symptoms of a cardiovascular complication, and/or he is not being treated for a cardiovascular complication.

Preferably, the patient is a patient who is receiving or about to receive cardiotoxic medication.

Cardiotoxic medication is known by the person skilled in the art. Cardiotoxic medication relates to any kind of drug treatment that can result in a cardiovascular complication. Particularly, cardiotoxic medication may cause cardiac cell damage (e.g. by induction of apoptosis), tissue damage, or may affect the cardiac conduction system.

Examples for cardiotoxic medication according to the present invention include antineoplastics (chemotherapeutics), tricyclic antidepressants, multiple sclerosis drugs, local anesthetics, interferon alpha, cocaine, sex hormones such as androgens or anabolics, and HIV-antiviral drugs.

Examples for antineoplastics according to the present invention include anthracyclines (e.g. daunorubicin, idarubicin, doxorubicin (adriamycin), and epirubicin), anthrachinone derivatives (e.g. mitoxantrone), acridine derivatives (e.g. amsacrine), arsenic trioxide, and antibodies for cancer therapy (particularly antibodies against HER2 and HER3, such as Trastuzumab (Herceptin)).

The antineoplastic mitoxantrone is also used in treatment of multiple sclerosis.

Examples for tricyclic antidepressants according to the present invention include amitriptyline, amoxapine, clomipramine, desipramine, doxepin, imipramine, nortriptyline, protriptyline, and trimipramine.

Examples for local anesthetics according to the present invention include cocaine and its derivatives, including benzocaine, procaine, tetracaine, lidocaine, etidocaine, prilocaine, mepivacaine, bupivacaine, ropivacaine, s-ropivacaine, atricaine, and fomocaine.

Also modifications of the above defined drugs are understood as cardiotoxic medication according to the present invention. Example for such modifications include pegylations or liposomal formulations, including so-called "stealth liposomes". Particular examples are liposomal doxorubicin (e.g. D-99), pegylated liposomal doxorubicin (e.g. Caelyx, Doxil), and liposomal daunorubicin (e.g. Daunoxome).

Examples for androgens are testosterone, 5-alpha-dihydrotestosterone, methyl testosterone, testosterone propionate, testosterone undecanoate, testosterone enanthate, fluoxymesterone, and mesterolone.

Anabolics include androgens which have been modified to reduce the androgenic effect of androgens while increasing their stimulating effect on protein formation. Examples for anabolics are nandrolone decanoate, clostebole acetate, and metenolone acetate, aromatase inhibitors, and beta-sympathomimetics (e.g. clenbuterol)

Examples for HIV-antiviral drugs are HIV protease inhibitors (e.g. amprenavir, indinavir, nelfinavir, ritonavir, saquinavir), nucleosidic reverse transcriptase inhibitors (NR-TIs, e.g. zidovudine (AZT), abacavir, didanosine, lamivudine, stavudine, zalcitabine), and non-nucleosidic reverse transcriptase inhibitors (NNRTIs, e.g. delavirdine, efavirenz, nevirapine).

HIV antiviral drugs are also included in HAART (highly active antiretroviral therapy) regimens. The classical HAART regimen comprises the simultaneous treatment with two NRTIs and one HIV protease inhibitors.

A detailed listing of cardiotoxic drugs used in HIV-treatment is given in Table 2 on page 1424 of Barbaro, G., (2002). Cardiovascular Manifestations of HIV Infection. Circulation, vol. 106, pp. 1420-1425.

Also considered as cardiotoxic medications are combinations of the mentioned drugs with other drugs, for example, chemotherapeutics may be combined with tricyclic antidepressants, local anesthetics, interferon-alpha, or androgens. As another example, multiple-sclerosis drugs may be combined with tricyclic antidepressants or interferons.

As known by the person skilled in the art, certain combinations or modifications show less cardiotoxic effects and present a choice for treatment, if the present invention indicates an increased or highly increased risk of cardiovascular complication. E.g. the above-mentioned pegylated drugs or liposomal formulations have been developed with purpose of reducing cardiotoxicity.

Cocaine and androgens are also known as drugs of abuse. For example, many HIV-patients are also drug abusers and initiating treatment with HIV antiviral drugs can trigger a cardiovascular complication. Similarly, athletes frequently use cocaine and/or androgens to increase their performance. Again, additional cardiotoxic medication may trigger a cardiovascular complication. Thus, the present invention also relates to diagnosing the risk of such patients of suffering from a cardiovascular complication as a consequence of additional cardiotoxic medication.

It is known to the person skilled in the art, under what circumstances a cardiovascular complication can be considered to occur "as a consequence" of the cardiotoxic medication. Particularly, a cardiovascular complication is considered to occur as a consequence of the cardiotoxic medication, if it occurs within a month, particularly a week, more particularly a day after onset of cardiotoxic medication.

Diagnosis according to the present invention is preferably done by use of a diagnostic means. A diagnostic means is any means that allows to measure the level, amount, or concentration of a substance of interest, particularly a peptide or polypeptide of interest, more particularly a cardiac hormone.

Methods and diagnostic means which can be used to determine the levels of the respective peptides are known to the person skilled in the art. These methods include microplate ELISA-based methods, fully-automated or robotic immunoassays (available for example on ELECSYS analyzers, Roche Diagnostics GmbH), CBA (an enzymatic Cobalt Binding Assay, available for example on Roche-Hitachi analyzers), and latex agglutination assays (available for example on Roche-Hitachi analyzers).

Furthermore, the person skilled in the art is familiar with different methods of measuring the level of a peptide or polypeptide. The term "level" relates to amount or concentration of a peptide or polypeptide in a patient or a sample taken from a patient.

The term "measuring" according to the present invention relates to determining the amount or concentration, preferably semi-quantitatively or quantitatively, of the nucleic acid, peptide, polypeptide, or other substance of interest. Measuring can be done directly or indirectly. Indirect measuring includes measuring of cellular responses, bound ligands, labels, or enzymatic reaction products.

In the context of the present invention, amount also relates to concentration. It is evident, that from the total amount of a substance of interest in a sample of known size, the concentration of the substance can be calculated, and vice versa.

Measuring can be done according to any method known in the art. Preferred methods are described in the following.

In a preferred embodiment, the method for measuring the level of a peptide or polypeptide of interest, particularly a cardiac hormone, comprises the steps of (a) contacting a cell capable of a cellular response to the peptide or polypeptide with the peptide or polypeptide for an adequate period of time, (b) measuring the cellular response.

In another preferred embodiment, the method for measuring the level of a peptide or polypeptide of interest, particularly a cardiac hormone, comprises the steps of (a) contacting a peptide or polypeptide with a suitable substrate for an adequate period of time, (b) measuring the amount of product.

In another preferred embodiment, the method for measuring the level of a peptide or polypeptide of interest, particularly a cardiac hormone, comprises the steps of (a) contacting a peptide or polypeptide with a specifically binding ligand, (b) (optionally) removing non-bound ligand, (c) measuring the amount of bound ligand.

Preferably, the peptide or polypeptide is contained in a sample, particularly a body fluid or tissue sample, and the amount of the peptide or polypeptide in the sample is measured.

Peptides and polypeptides (proteins) can be measured in tissue, cell, and body fluid samples, i.e. preferably in vitro. Preferably, the peptide or polypeptide of interest is measured in a body fluid sample.

A tissue sample according to the present invention refers to any kind of tissue obtained from the dead or alive human or animal body. Tissue samples can be obtained by any method known to the person skilled in the art, for example by biopsy or curettage.

Body fluids according to the present invention may include blood, blood serum, blood plasma, lymphe, cerebral liquor, saliva, and urine. Particularly, body fluids include blood, blood serum, blood plasma, and urine. Samples of body fluids can be obtained by any method known in the art.

Methods to obtain cell samples include directly preparing single cells or small cell groups, dissociating tissue (e.g. using trypsin), and separating cells from body fluids, e.g. by filtration or centrifugation. Cells according to the present invention comprise also platelets and other non-nuclear cells, e.g. erythrocytes.

If necessary, the samples may be further processed. Particularly, nucleic acids, peptides or polypeptides may be purified from the sample according to methods known in the art, including filtration, centrifugation, or extraction methods such as chloroform/phenol extraction.

For measuring cellular responses, the sample or processed sample is added to a cell culture and an internal or external cellular response is measured. The cellular response may include the expression of a reporter gene or the secretion of a substance, e.g. a peptide, polypeptide, or a small molecule.

Other preferred methods for measurement may include measuring the amount of a ligand binding specifically to the peptide or polypeptide of interest. Binding according to the present invention includes both covalent and non-covalent binding.

A ligand according to the present invention can be any peptide, polypeptide, nucleic acid, or other substance binding to the peptide or polypeptide of interest. It is well known that peptides or polypeptides, if obtained or purified from the human or animal body, can be modified, e.g. by glycosylation. A suitable ligand according to the present invention may bind the peptide or polypeptide also via such sites.

Preferably, the ligand should bind specifically to the peptide or polypeptide to be measured. "Specific binding" according to the present invention means that the ligand should not bind substantially to ("cross-react" with) another peptide, polypeptide or substance present in the sample investigated. Preferably, the specifically bound protein or isoform should be bound with at least 3 times higher, more preferably at least 10 times higher and even more preferably at least 50 times higher affinity than any other relevant peptide or polypeptide.

Non-specific binding may be tolerable, particularly if the investigated peptide or polypeptide can still be distinguished and measured unequivocally, e.g. according to its size on a Western Blot, or by its relatively higher abundance in the sample.

Binding of the ligand can be measured by any method known in the art. Preferably, the method is semi-quantitative or quantitative. Suitable methods are described in the following.

First, binding of a ligand may be measured directly, e.g. by NMR or surface plasmon resonance.

Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot).

For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for an detectable, preferably measurable amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand.

Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.)

The ligand or substrate may also be "tagged" with one or more tags as known in the art. Such tags may then be targets for higher order ligands. Suitable tags include biotin, digoxigenin, His-Tag, Glutathione-S-Transferase, FLAG, GFP, myc-tag, influenza A virus haemagglutinin (HA), maltose binding protein, and the like. In the case of a peptide or polypeptide, the tag is preferably at the N-terminus and/or C-terminus.

Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels.

Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemiluminescence, which can be measured according to methods known in the art (e.g. using a light-sensitive film or a suitable camera system). As for measuring the enzymatic reaction, the criteria given above apply analogously.

Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated.

Typical radioactive labels include 35S, 125I, 32P, 33P and the like. A radioactive label can be detected by any method known and appropriate, e.g. a light-sensitive film or a phosphor imager.

Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immunoassay (DELFIA), scintillation proximity assay (SPA), turbidimetry, nephelometry, latex-enhanced turbidimetry or nephelometry, solid phase immune tests, and mass spectrometry such as SELDI-TOF, MALDI-TOF, or capillary electrophoresis-mass spectrometry (CE-MS). Further methods known in the art (such as gel electrophoresis, 2D gel electrophoresis, SDS polyacrylamide gel electrophoresis (SDS-PAGE), Western Blotting), can be sued alone or in combination with labeling or other detection methods as described above.

Preferred ligands include antibodies, nucleic acids, peptides or polypeptides, and aptamers, e.g. nucleic acid or peptide aptamers. Methods to such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduces into the nucleic acids, peptides or polypeptides. These derivatives can then be tested for binding according to screening procedures known in the art, e.g. phage display.

The term "antibody" as used herein includes both polyclonal and monoclonal antibodies, as well as fragments thereof, such as Fv, Fab and F(ab)2 fragments that are capable of binding antigen or hapten.

In another preferred embodiment, the ligand, preferably chosen from the group consisting of nucleic acids, peptides, polypeptides, more preferably from the group consisting of nucleic acids, antibodies, or aptamers, is present on an array.

Said array contains at least one additional ligand, which may be directed against a peptide, polypeptide or a nucleic acid of interest. Said additional ligand may also be directed against a peptide, polypeptide or a nucleic acid of no particular interest in the context of the present invention. Preferably, ligands for at least three, preferably at least five, more preferably at least eight peptides or polypeptides of interest in the context of the present invention are contained on the array.

According to the present invention, the term "array" refers to a solid-phase or gel-like carrier upon which at least two compounds are attached or bound in one-, two- or three-dimensional arrangement. Such arrays (including "gene chips", "protein chips", antibody arrays and the like) are generally known to the person skilled in the art and typically generated on glass microscope slides, specially coated glass slides such as polycation-, nitrocellulose- or biotin-coated slides, cover slips, and membranes such as, for example, membranes based on nitrocellulose or nylon.

The array may include a bound ligand or at least two cells expressing each at least one ligand.

It is also contemplated to use "suspension arrays" as arrays according to the present invention (Nolan J P, Sklar L A. (2002). Suspension array technology: evolution of the flat-array paradigm. Trends Biotechnol. 20(1):9-12). In such suspension arrays, the carrier, e.g. a microbead or microsphere, is present in suspension. The array consists of different microbeads or microspheres, possible labeled, carrying different ligands.

The invention further relates to a method of producing arrays as defined above, wherein at least one ligand is bound to the carrier material in addition to other ligands.

Methods of producing such arrays, for example based on solid-phase chemistry and photo-labile protective groups, are generally known (U.S. Pat. No. 5,744,305). Such arrays can also be brought into contact with substances or substance libraries and tested for interaction, for example for binding or change of confirmation. Therefore, arrays comprising a peptide or polypeptide as defined above may be used for identifying ligands binding specifically to said peptides or polypeptides.

The method according to the present invention comprises the step of diagnosing the risk of the patient by comparing the measured level to known levels associated with different grades of risk in a patient.

The person skilled in the art is able to determine known levels of cardiac hormones which are associated with different grades of risk of suffering from a cardiovascular complication as a consequence of cardiotoxic medication.

According to the present invention, the term "risk" relates to the probability of a particular incident, more particularly a cardiovascular complication, to take place. The grade of risk can be increased, highly increased, or very highly increased. The grade of risk can also not be increased. "No increased risk" means that there is apparently no risk of suffering from a cardiovascular complication as a consequence of cardiotoxic medication.

Guidance as to what levels are associated with which grade of risk can be drawn from levels of cardiac hormones known to be associated with the presence or severity of a cardiovascular disease. For example, based on a 97.5 percentile obtained in individuals below the age of 50, a plasma level of 125 pg/ml of NT-proBNP was considered a normal level (see Example 3). Higher levels of NT-proBNP correlate for example with the level of symptoms according to the NYHA classification and with the level of impairment of LVEF. The term "plasma level" relates to levels of NT-proBNP measured in blood plasma.

Below, plasma levels of NT-proBNP are given which are typically considered to be associated with the indicated grades of risk of suffering from a cardiovascular complication as a consequence of cardiotoxic medication.

It is evident, that the levels given below can serve only as a first classification of the risk of a patient. For example, the risk is also dependent on the spare pumping capacity of heart of the particular patient.

The value of the known level may also be chosen according to the desired sensitivity or specificity of diagnosis. The higher the desired sensitivity, the lower is the specificity of diagnosis and vice versa. For example, the higher the known level of NT-proBNP that is chosen to define the risk, the higher will be the specificity of diagnosis. However, the sensitivity of diagnosis will be lower.

Furthermore, the person skilled in the art is able to determine other relevant levels from the Examples shown further below, particularly levels which are relevant in certain patient populations, such as elderly patients or patients with a increased or decreased levels of markers for thyroid function (e.g. TSH or FT4).

Typically, a plasma level of less than 50 pg/ml of NT-proBNP is associated with no increased risk of suffering from a cardiovascular complication as a consequence of cardiotoxic medication. Particularly, in male patients a plasma level of less than approximately 60 to 100 pg/ml is associated with no increased risk, whereas in female patients a plasma level of less than approximately 120 to 150 pg/ml is associated with no increased risk. The average value is 125 pg/ml.

Typically, a plasma level higher that the plasma level for no increased risk but lower than 1000 pg/ml of NT-proBNP is associated with an increased risk of suffering from a cardiovascular complication as a consequence of cardiotoxic medication.

Typically, a plasma level from 1000 to 5000 pg/ml of NT-proBNP is associated with a highly increased risk of suffering from a cardiovascular complication as a consequence of cardiotoxic medication.

Typically, a plasma level of more than 5000 pg/ml of NT-proBNP is associated with a very highly increased risk of suffering from a cardiovascular complication as a consequence of cardiotoxic medication.

Once the risk in a patient has been diagnosed, it may have consequences for the subsequent treatment as described below. The grades of risk mentioned below particularly refer to the grades of risk associated with the above described levels of NT-proBNP.

If a method according to the present invention indicates no increased risk, then treatment may be continued as planned.

If a method according to the present invention indicates an increased risk, then treatment may be adapted. Preferably, treatment will be accompanied by further measuring of the level of the cardiac hormones of the invention and by further diagnosis, such as electrocardiography, echocardiography, or any other suitable methods known to the skilled cardiologist. The dose of cardiotoxic medication may be reduced and/or a less cardiotoxic type of medication may be chosen for treatment. Furthermore, adapting treatment may include measures such as restriction of salt intake, regular moderate exercise, avoidance of non-steroidal anti-inflammatory agents, providing influenzal and pneumococcal immunization, administering drugs such as diuretics (including co-administration of more than one diuretic), ACE inhibitors, β-adrenergic blockers, angiotensin-receptor blockers, digitalis and any other measures known and deemed appropriate by the person skilled in the art. Therefore, the present invention also provides a method of treating a patient who is receiving or about to receive cardiotoxic medication.

If a method according to the present invention indicates a highly increased risk, then treatment may be adapted as described for increased risk. However, it may also be reconsidered if any cardiotoxic medication can be tolerated.

If a method according to the present invention indicates a very highly increased risk, then treatment may be adapted as described for highly increased risk. However, also immediate hospitalization and/or intensive cardiac treatment may be considered.

In another embodiment, the present invention relates to a method for deciding on treatment of a patient with cardiotoxic medication, comprising the steps of (a) measuring, preferably in vitro, the level of a cardiac hormone, (b) diagnosing the risk of the patient of suffering from a cardiovascular complication as a consequence of the planned treatment by comparing the measured level of the cardiac hormone to known levels associated with different grades of risk in a patient, (c) optionally initiating an examination of the patient by a cardiologist, (d) recommending the initiation of the treatment or refraining from the treatment, optionally in consideration of the result of the patient's examination by the cardiologist. Preferably, initiating an examination by a cardiologist and/or refraining from treatment is recommended if the method indicates the presence of a risk of suffering from a cardiovascular complication as a consequence of the cardiotoxic medication. It is evident that the method may be adapted according to all embodiments or preferred aspects of the invention mentioned in this specification.

SPECIFIC EMBODIMENTS

Example 1

Measurement of NT-proBNP

NT-proBNP was determined by an electrochemoluminescence immunoassay (ELECSYS proBNP sandwich immuno assay; Roche Diagnostics, Mannheim, Germany) on ELECSYS 2010. The assay works according to the electrochemoluminescence sandwich immunoassay principle. In a first step, the biotin-labelled IgG (1-21) capture antibody, the ruthenium-labelled F(ab')2 (39-50) signal antibody and 20 microliters of sample are incubated at 37° C. for 9 minutes. Afterwards, streptavidin-coated magnetic microparticles are added and the mixture is incubated for additional 9 minutes. After the second incubation, the reaction mixture is transferred to the measuring cell of the system where the beads are magnetically captured onto the surface of an electrode. Unbound label is removed by washing the measuring cell with buffer.

In the last step, voltage is applied to the electrode in the presence of a tri-propylamine containing buffer and the resulting electrochemoluminescent signal is recorded by a photomultiplier. All reagents and samples are handled fully automatically by the ELECSYS instrument. Results are determined via a calibration curve which is instrument-specifically generated by 2-point calibration and a master curve provided via the reagent barcode. The test was performed according to the instructions of the manufacturer.

Example 2

Analysis

Blood for hormone analysis was sampled in EDTA-tubes containing 5000 U aprotinine (Trasylol, Beyer, Germany) and Lithium-Heparin-tubes (for clinical chemistry), as appropriate, Blood and urine samples were immediately spun for 10 min. at 3400 rpm at 4° C. Supernatants were stored at −80° C. until analysis.

Determination of NT-proANP

NT-proANP was determined by a competitive-binding radioimmuno assay with magnetic solid phase technique in a modification of Sundsfjord, J. A., Thibault, G., et al. (1988). Identification and plasma concentrations of the N-terminal fragment of proatrial natriuretic factor in man. J Clin Endocrinol Metab 66:605-10, using the same rabbit-anti-rat proANP polyclonal serum, human proANP (1-30) from Peninsula Lab (Bachem Ltd, St. Helene, UK) as the standard, and iodined, proANP 1-30 purified by HPLC for radio labelling. In order to achieve high sensitivity and good precision, Dynabeads M280 with sheep-anti-rabbit IgG (Dynal Biotech, Oslo, Norway) as solid phase and second antibody were used. The coefficient of variance, at 425, 1163, and 2490 pmol *1-1 was 7.5, 3.7, and 3.4%, respectively. The detection limit was 30 pmol/l.

Determination of NT-proBNP

NT-proBNP was determined by an electrochemoluminescence immunoassay (ELECSYS proBNP sandwich immuno assay; Roche Diagnostics, Basel, Switzerland) on ELECSYS 2010 (Mueller, T., Gegenhuber, A. (2003). Comparison of the Biomedica NT-proBNP enzyme immuno assay and the Roche NT-proBNP chemiluminescence immuno assay: implications for the prediction of symptomatic and asymptomatic structural heart disease. Clin. Chem. 49:976-9), see also Example 1. The mean intra-assay variance was 4.3% (range: 2.7 to 5.9% for plasma samples with a concentration between 7.6 to 2732 pmol *1-1 with an interassay variance of 3.2%. The lower detection limit was 0.6 pmol *1-1.

Example 3

A Study of NT-proBNP Levels in Blood Donors

A total of 1981 blood donors were recruited from the blood transfusion service of the University of Mainz, Germany. The majority of the blood donors were repeat donors and repeat donors do receive a physical examination at yearly interval. Based on this examination all blood donors included into the study were considered clinically healthy. At the time of blood donation hemoglobin levels as well as creatinin levels were taken. All determinations were done before blood donation. The study was conducted according to the Declaration of Helsinki and was approved by a local ethical committee.

As depicted in FIG. 1, individual NT-proBNP values are plotted in relation to age and sex. As becomes evident from FIG. 7, NT-proBNP levels (median) were higher in women than in men. Outliers were more frequently observed in elderly individuals (above the age of 50 years) whereas in younger individuals (below 50 years of age) individual determinations clustered. Age and sex-related reference values based on the 97.5 percentile were calculated and found to be 84.2 pg/ml for males and 146.2 pg/ml for females respectively under the age of 50 years (Table 1).

TABLE 1

Age group classified and gender-specific NT-proBNP levels in blood donors

| | Age (y) | | | | | | | | | | | |
|---|---|---|---|---|---|---|---|---|---|---|---|---|
| | 18-49 | 18-49 | 18-29 | 18-29 | 30-39 | 30-39 | 40-49 | 40-49 | 50-59 | 50-59 | >60 | >60 |
| | | | | | Gender | | | | | | | |
| | m | f | m | f | m | f | m | f | m | f | m | f |
| N | 964 | 574 | 278 | 232 | 379 | 194 | 307 | 148 | 211 | 94 | 110 | 28 |
| Median | 20.0 | 39.3 | 20.0 | 37.0 | 20.0 | 36.9 | 20.0 | 49.8 | 27.4 | 65.8 | 42.0 | 61.4 |
| 97.5% Percentile | 84.2 | 146.2 | 64.7 | 129.7 | 88.1 | 132.2 | 94.6 | 230.7 | 178.5 | 270.3 | 278.0 | 261.7 |

N, number of blood donors, m, male; f, female.

A second sample at an approximately 12 months interval was collected from all individuals who were outside the above range as can be seen from Table 2, the majority of samples remained outside the respective reference range suggesting that these elevated values were constant findings. A small subset of individuals with initial values outside the range described in the second sample has values that were considered to be within the defined reference ranges.

Figure 2:
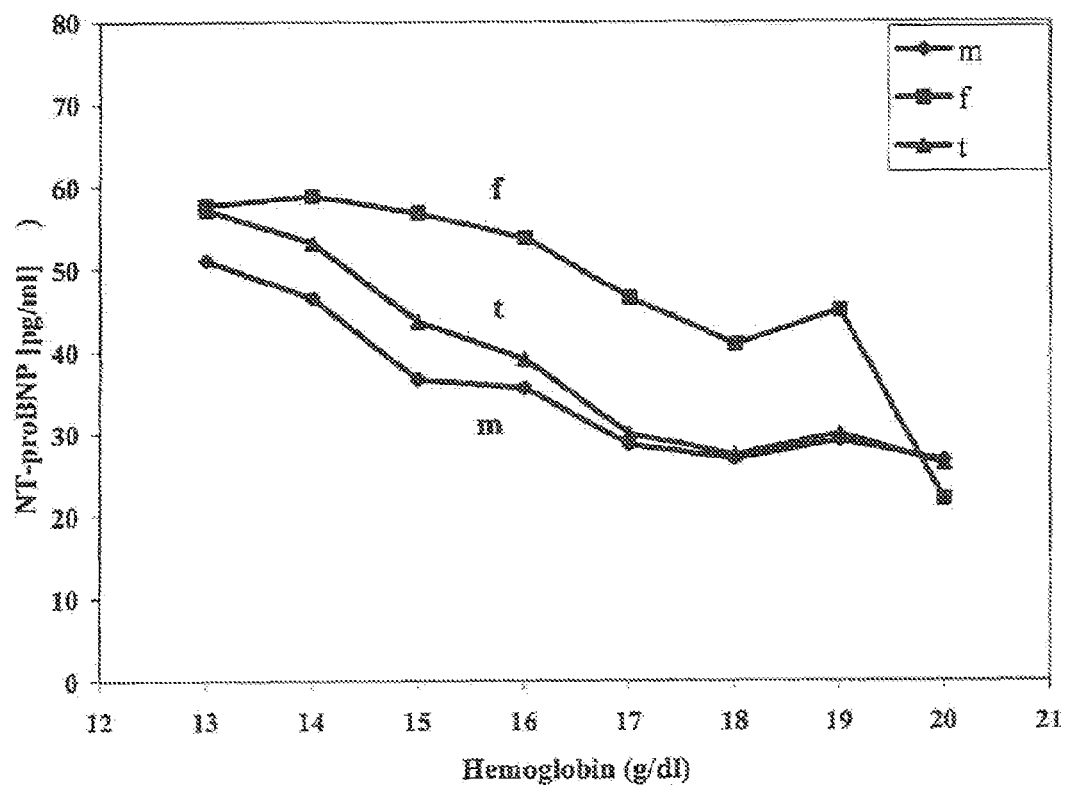
FIG. 2: NT-proBNP levels in blood donors and the relation to hemoglobin levels. m, male (diamonds); f, female (squares), t, total (triangles).

In order to assess whether NT-proBNP values were independent on hemoglobin levels, hemoglobin concentrations were determined in males and females and found to be in average 1.5 g/ml lower in females than in males (Table 2). Hemoglobin levels did not depend on age.

levels did not explain the different concentrations found for NT-proBNP between males and females. It also became apparent that NT-proBNP levels were in fact hemoglobin-dependent, NT-proBNP levels increased with decreasing hemoglobin concentration (FIG. 2).

In a subset of individuals creatinin levels were compared to NT-proBNP levels. In the group studied creatinin levels were in the normal range for all individuals tested. Creatinin levels did not increase with age, in contrast, NT-proBNP levels increased with age suggesting that kidney function might not trigger increase of NT-proBNP with increasing age (Table 3).

TABLE 3

Age-group and gender-specific NT-proBNP levels (median) in blood donors in relation to creatinin levels.

| Age distribution | N | Crea [mg/dL] median total | NT-proBNP [pg/ml] median | N | Crea [mg/dL] median male | NT-proBNP [pg/ml] median | N | Crea [mg/dL] median female | NT-proBNP [pg/ml] median |
|---|---|---|---|---|---|---|---|---|---|
| total | 880 | 0.79 | 25.3 | 528 | 0.80 | 20.0 | 352 | 0.66 | 47.0 |
| ≦20 | 7 | 0.81 | 20.0 | 2 | 0.90 | 20.0 | 5 | 0.72 | 20.0 |
| 21-30 | 192 | 0.78 | 20.0 | 109 | 0.87 | 20.0 | 83 | 0.66 | 43.4 |
| 31-40 | 264 | 0.78 | 22.0 | 155 | 0.80 | 20.0 | 109 | 0.66 | 37.2 |
| 41-50 | 205 | 0.79 | 25.5 | 121 | 0.89 | 20.0 | 84 | 0.66 | 53.2 |
| 51-60 | 157 | 0.80 | 37.6 | 100 | 0.83 | 25.3 | 57 | 0.67 | 61.4 |
| 61-65 | 55 | 0.79 | 43.7 | 41 | 0.83 | 41.6 | 14 | 0.63 | 72.3 |

Crea, creatinin; N, number of blood donors.

TABLE 2

Follow-up (12 month) of N = 48 blood donors with elevated NT-proBNP levels.

| | NT-proBNP Return to normal range | NT-proBNP Remains Increased |
|---|---|---|
| N male | 7 | 14 |
| N female | 7 | 20 |
| N total | 14 | 34 |

When NT-proBNP values were compared between males and females at the same hemoglobin levels and in age-matched groups there was still a difference between males and females in terms of NT-proBNP levels suggesting that hemoglobin The study was initiated to determine normal and reference NT-proBNP values in an apparently healthy population. As shown, individual NT-proBNP levels clustered up to the age of 50 years with only few outliers. This finding is consistent with the assumption that cardiac and specifically cardiovascular diseases are rare in this age group, therefore values obtained in individuals below the age of 50 were considered based on a 97.5 percentile as normal values. These values were also found to be different between males and females. It could also be shown that in fact hemoglobin levels affected the level of NT-proBNP in that individuals with lower hemoglobin had higher NT-proBNP levels. When looking at the same hemoglobin levels there were still differences between men and women. Thus, hemoglobin levels did not explain for the differences in NT-proBNP levels seen between both sexes.

This study showed that a substantial number of individuals had NT-proBNP levels exceeding the 97.5 percentile of individuals below the age of 50. The number of these outliers increased with age. Determination of NT-proBNP levels was done by the ELECSYS immunoassay as described in Example 1.

Example 4

A Study of NT-proBNP Levels in Patients Presenting with Suspected Cardiac Disorders A total of 473 patients presenting to 18 cardiologists were recruited for the study. They received a medical history, a physical examination and an echocardiogram where left ventricular ejection fraction was recorded. In addition, 10 ml of blood was drawn, centrifuged and stored at −20° C. until analyzed. Major demographic variables of the patients included in this study are depicted in Table 4. The study was approved by a local ethical committee and conducted according to the Declaration of Helsinki.

TABLE 4

Characteristics of the study population of patients presenting with suspected cardiac disorders t, total; m, male; f, female.

| | Patients | | |
|---|---|---|---|
| | t | m | f |
| N | 473 | 258 | 215 |
| Age [median] | 66.0 | 64.5 | 68.0 |
| Symptoms & Indication | N | N | N |
| Arterial Hypertension | 280 | 144 | 136 |
| Blood pressure, systolic | 182 | 96 | 86 |
| Blood pressure, diastolic | 78 | 34 | 44 |
| Dyspnea | 208 | 102 | 106 |
| Edema | 45 | 20 | 25 |
| Arrhythmia | 32 | 16 | 16 |
| Angina Pectoris | 122 | 64 | 58 |
| AMI Anamnese | 165 | 59 | 106 |
| Classification | N | N | N |
| NYHA I | 308 | 176 | 132 |
| NYHA II | 112 | 52 | 60 |
| NYHA III | 50 | 27 | 23 |
| NYHA IV | 3 | 3 | 0 |
| NYHA II-IV | 165 | 82 | 83 |
| LVEF <30% | 27 | 18 | 9 |
| LVEF 30-50% | 86 | 56 | 30 |
| LVEF >50% | 360 | 184 | 176 |

The following tests were done in all or the majority of the patients: Creatinin levels, TSH, FT4, and NT-proBNP. The tests were conducted according to the instructions of the manufacturer (Roche Diagnostics, Mannheim, Germany). NT-proBNP was analyzed using a newly developed immunoassay (Roche Diagnostics, Mannheim, Germany) using an ELECSYS 2010 instrument (see Example 1).

Significancies were calculated based on Wilcoxon Score method and Pearson Chi-Square test: Significance is present at p-values *P<0.05, P<0.01, *P<0.001. The probability of error should not exceed 5%.

Patients were separated into three groups according to left ventricular injection fraction (LVEF), namely under 30% LVEF, 30-50% LVEF, and over 50% LVEF. The patients were also graded according to NYHA classification in grade I-IV.

Figure 3:
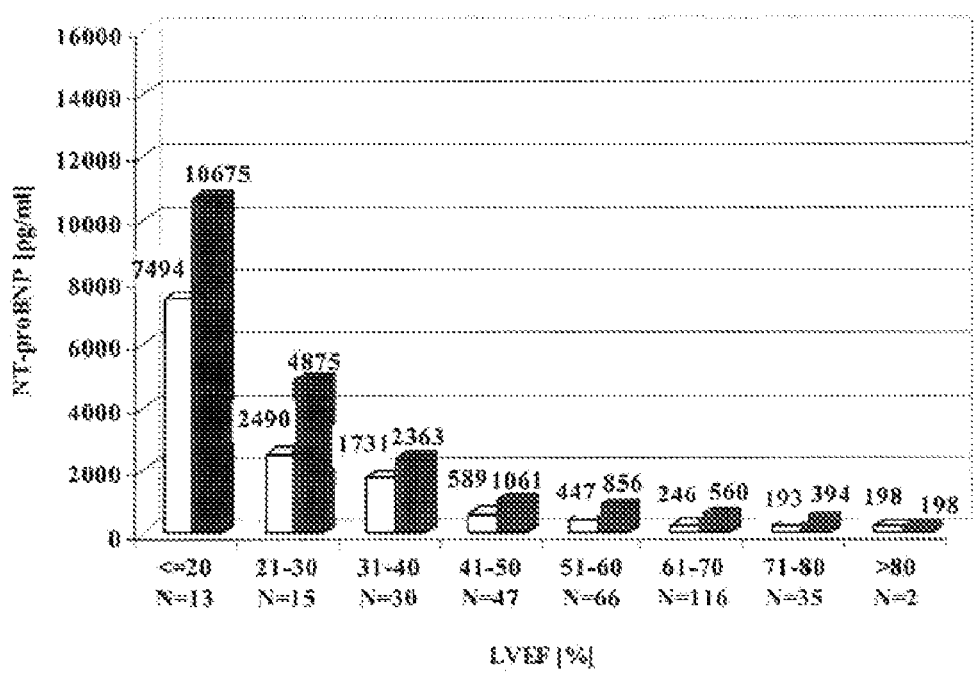
FIG. 3: NT-proBNP levels in males according LVEF.
Figure 4:
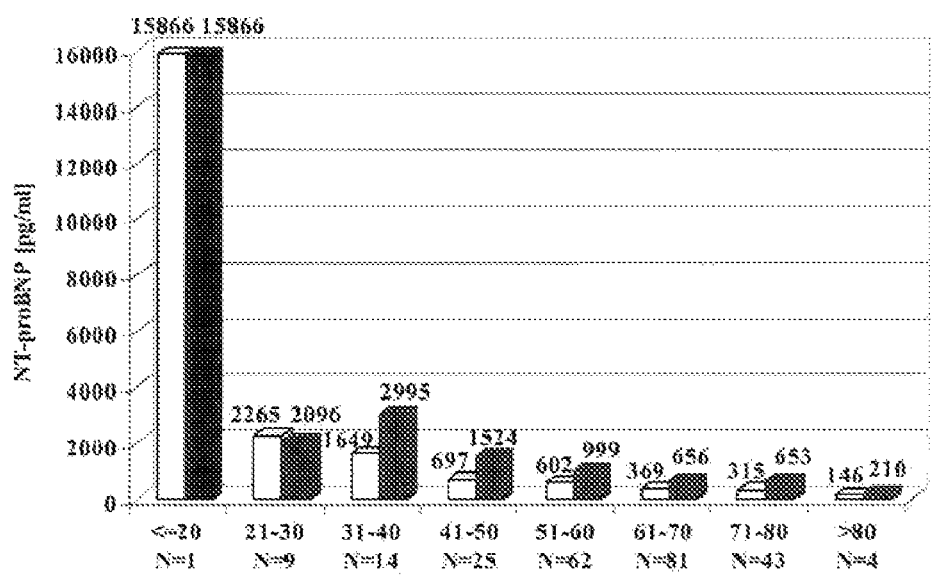
FIG. 4: NT-proBNP levels in female according LVEF.

As depicted in Table 5, NT-proBNP levels were recorded based on the level of left ventricular ejection fraction and based on symptoms. The majority of individuals had increased NT-proBNP levels if a cut-off of 84 pg/ml for males and 146 pg/ml for females were used, this discriminates between normal and abnormal cardiac function (see Example 1). The mean NT-proBNP levels increased with the level of symptoms as assessed by NYHA classification and with the level of impaired ejection fraction as measured by echo. The dependency of NT-proBNP on left ventricular injection fraction is also summarized in FIGS. 3 and 4 for males and females respectively. As can be seen from the figures, NT-proBNP levels (median) increased with decreasing ejection fraction.

TABLE 5

NT-proBNP levels in patients according to LVEF and NYHA classification.

| | | LVEF | | |
|---|---|---|---|---|
| | | ≤30% | 30-50% | >50% |
| NYHA | N, total | 27 | 86 | 361 |
| I | N | 2 | 27 | 280 |
| | NT-proBNP [pg/ml] mean | 2848.8 | 506.4 | 302.1 |
| II | N | 6 | 36 | 70 |
| | NT-proBNP [pg/ml] mean | 1896.5 | 862.5 | 488.5 |
| III | N | 16 | 23 | 11 |
| | NT-proBNP [pg/ml] mean | 2467.9 | 1946.3 | 698.4 |
| IV | N | 3 | 0 | 0 |
| | NT-proBNP [pg/ml] mean | 16223.2 | 0 | 0 |

As shown in Table 6, only a minority of individuals recruited for the study in the cardiologists centers had normal NT-proBNP levels based on cut-offs made from a study in blood donors below the age of 50 (see Example 3). Normal NT-proBNP values clustered in individuals with unimpaired left ventricular fraction and without symptoms, only few outliers were identified.

TABLE 6

Patients with NT-proBNP levels below cut-off (male: 84 pg/ml; female 155 pg/ml) with reduced LVEF.

| | | LVEF | | | | | |
|---|---|---|---|---|---|---|---|
| | | ≤30% | | 30-50% | | >50% | |
| | | | | N, total | | | |
| | | 27 | | 86 | | 361 | |
| NYHA | | male | female | male | female | male | female |
| I | N | 0 | 0 | 2 | 0 | 29 | 11 |
| II | N | 0 | 0 | 0 | 3 | 1 | 5 |
| III | N | 0 | 0 | 0 | 0 | 0 | 0 |
| IV | N | 0 | 0 | 0 | 0 | 0 | 0 |

A total of 32 individuals had atrial fibrillation as indicated by electrocardiogram (ECG) while the majority of individuals had no evidence of atrial fibrillation. As can be seen from Table 7, median values in the atrial fibrillation group were higher than in the non-atrial fibrillation group. Major demographic valuables for these patient groups are depicted. Individuals who had no atrial fibrillation had more frequently a history of myocardial infarction and Angina Pectoris. The data suggest that atrial fibrillation represents an independent contributor for elevated NT-proBNP levels (P: 0.0002).

TABLE 7

NT-proBNP levels in patients with atrial fibrillation compared to patients without atrial fibrillation.

|  | Atrial Fibrillation | | No Atrial Fibrillation | | p-Value |
|---|---|---|---|---|---|
| N, total | 32 | | 442 | | |
| Age [median] | 68.0 | | 66.0 | | |
| NT-proBNP [pg/ml] median | 1055.0 | | 401.7 | | 0.0002 *** |
|  | N | % | N | % | |
| NYHA I | 22 | 68.8% | 287 | 64.9% | >=0.05 |
| NYHA II | 6 | 18.8% | 106 | 24.0% | >=0.05 |
| NYHA III | 4 | 12.5% | 46 | 10.4% | >=0.05 |
| NYHA IV | 0 | 0 | 3 | 0.7% | >=0.05 |
| LVEF <30% | 0 | 0 | 27 | 6.1% | >=0.05 |
| LVEF 30-50% | 6 | 18.8% | 80 | 18.1% | >=0.05 |
| LVEF >50% | 26 | 81.3% | 335 | 75.8% | >=0.05 |
| Arterial Hypertension | 13 | 40.6% | 267 | 60.4% | >=0.05 |
| Blood pressure, systolic | 12 | 37.5% | 170 | 38.5% | >=0.05 |
| Blood pressure, diastolic | 7 | 21.9% | 71 | 16.1% | >=0.05 |
| Dyspnea | 13 | 40.6% | 195 | 44.1% | >=0.05 |
| Edema | 3 | 9.4% | 42 | 9.5% | >=0.05 |
| Angina Pectoris | 6 | 18.8% | 116 | 26.2% | >=0.05 |
| AMI Anamnese | 0 | 0 | 78 | 17.6% | >=0.0154* |

A total of 78 individuals had a history of myocardial infarction (MI) while the majority had no history of MI. Individuals with the history of myocardial infarction had higher NT-proBNP levels than those who had no history of MI (Table 8).

TABLE 8

NT-proBNP levels in patients with myocardial infect anamnesis (AMI) in comparison to patients without AMI anamnesis.

|  | AMI | | No AMI | | p-Value |
|---|---|---|---|---|---|
| N, total | 78 | | 381 | | |
| Age [median] | 67.5 | | 66.0 | | |
| NT-proBNP [pg/ml] median | 797.0 | | 370.8 | | 0.0001 *** |
|  | N | % | N | % | |
| NYHA I | 33 | 42.3% | 266 | 69.8% | 0.001 ** |
| NYHA II | 31 | 39.7% | 79 | 20.7% | 0.001 ** |
| NYHA III | 14 | 17.9% | 33 | 8.7% | 0.001 ** |
| NYHA IV | 0 | 0 | 3 | 0.8% | 0.001 ** |
| LVEF <30% | 7 | 9.0% | 19 | 5.0% | 0.001 ** |
| LVEF 30-50% | 37 | 47.4% | 47 | 12.3% | 0.001 ** |
| LVEF >50% | 34 | 43.6% | 315 | 82.7% | 0.001 ** |
| Arterial Hypertension | 45 | 57.7% | 234 | 61.4% | >=0.05 |
| Blood pressure, systolic | 21 | 26.9% | 154 | 40.4% | >=0.05 |
| Blood pressure, diastolic | 4 | 5.1% | 72 | 18.9% | >=0.05 |
| Dyspnea | 51 | 65.4% | 156 | 40.9% | 0.0001* ** |
| Edema | 10 | 12.8% | 35 | 9.2% | >=0.05 |
| Angina Pectoris | 32 | 41.0% | 89 | 23.4% | 0.0015** |
| Arrhythmia | 0 | 0 | 27 | 7.1% | 0.0154* |

NT-proBNP values were higher in individuals with a history of angina pectoris than in those who had no history of angina pectoris (Table 9). Patients with a history of angina pectoris were not frequently symptomatic, had more frequently heart diseases and more frequently of history of myocardial infarction (Table 8).

TABLE 9

NT-proBNP levels in patients with angina pectoris in comparison to patients without angina pectoris.

|  | Angina Pectoris | No Angina Pectoris | p-Value |
|---|---|---|---|
| N, | 122 | 33.5 | |
| Age [median] | 69.5 | 64.0 | |
| NT-proBNP [pg/ml] median | 589.5 | 369.3 | 0.009 ** |

TABLE 9-continued

NT-proBNP levels in patients with angina pectoris in comparison to patients without angina pectoris.

|  | N | % | N | % |  |
| --- | --- | --- | --- | --- | --- |
| NYHA I | 55 | 45.1% | 242 | 72.2% | 0.00001 *** |
| NYHA II | 50 | 41.0% | 60 | 17.9% | 0.00001 *** |
| NYHA III | 16 | 13.1% | 31 | 9.3% | 0.00001 *** |
| NYHA IV | 1 | 0.8% | 2 | 0.6% | 0.00001 *** |
| LVEF <30% | 6 | 4.9% | 12 | 3.6% | >=0.05 |
| LVEF 30-50% | 30 | 24.6% | 62 | 18.5% | >=0.05 |
| LVEF >50% | 86 | 70.5% | 261 | 77.9% | >=0.05 |
| Arterial Hypertension | 87 | 71.3% | 191 | 57.0% | 0.0056** |
| Blood pressure, systolic | 45 | 36.9% | 129 | 38.5% | >=0.05 |
| Blood pressure, diastolic | 18 | 14.8% | 57 | 17.0% | >=0.05 |
| Dyspnea | 81 | 66.4% | 125 | 37.3% | 0.001*** |
| Edema | 20 | 16.4% | 25 | 7.5% | 0.0042** |
| AMI Anamnese | 32 | 26.2% | 46 | 13.7% | 0.0015** |
| Arrhytmia | 6 | 4.9% | 21 | 6.3% | >=0.05 |

Creatinin was determined in 470 individuals. Only 152 individuals had creatinin levels in the normal range, 318 were outside of the normal range. Individuals with elevated creatinin levels had higher NT-proBNP levels than those with normal creatinin levels. Demographic variables suggest that individuals with elevated creatinin levels had more frequently a history of myocardial infarction. The data suggest that impaired kidney function per se might contribute the elevation of NT-proBNP levels when patients with a history of MI (AMI) were excluded from assessment (Table 9).

In a subgroup of 306 individuals thyroid function was measured. Based on TSH and FT4 levels the patients were classified in individuals with normal thyroid function and in those with abnormal thyroid function. The majority of the individuals with abnormal thyroid function had elevated TSH levels, but normal FT4, suggesting compensated hypothyroid function. Median NT-proBNP levels were higher in individuals with abnormal thyroid function than in those with normal thyroid function. This suggest that thyroid dysfunction represents a contributor to elevated NT-proBNP levels most likely associated with impaired cardiac function through impaired thyroid function (Table 11).

TABLE 10

NT-proBNP levels in patients with elevated creatinin levels.

|  | Creatinin | | p-Value |
| --- | --- | --- | --- |
|  | normal | elevated |  |
|  | 0.66-1.1 mg/dl | >1.1 mg/dl |  |
| N, total | 140 | 253 |  |
| Age [median] | 66.0 | 65.0 |  |
| NT-proBNP [pg/ml] median | 289.7 | 456.5 | 0.0003 *** |

|  | N | % | N | % |  |
| --- | --- | --- | --- | --- | --- |
| NYHA I | 99 | 70.7% | 176 | 69.6% | >=0.05 |
| NYHA II | 31 | 22.1% | 49 | 19.4% | >=0.05 |
| NYHA III | 10 | 7.1% | 25 | 9.9% | >=0.05 |
| NYHA IV | 0 | 0 | 3 | 1.2% | >=0.05 |
| LVEF ≦30% | 5 | 3.6% | 15 | 5.9% | >=0.05 |
| LVEF 30-50% + >50% | 135 | 96.4% | 238 | 94.1% | >=0.05 |
| Arterial Hypertension | 92 | 65.7% | 141 | 55.7% | >=0.05 |
| Blood pressure, systolic | 66 | 47.1% | 94 | 37.2% | >=0.05 |
| Blood pressure, diastolic | 32 | 22.9% | 41 | 16.2% | >=0.05 |
| Dyspnea | 57 | 40.7% | 97 | 38.3% | >=0.05 |
| Edema | 16 | 11.4% | 19 | 7.5% | >=0.05 |
| Angina Pectoris | 31 | 22.1% | 58 | 22.9% | >=0.05 |
| Arrhytmia | 8 | 5.7% | 24 | 9.5% | >=0.05 |

TABLE 11

NT-proBNP levels in patients with regular thyroid function in comparison to patients with thyroid dysfunction.

|  | Euthyreose | | Thyroid Dysfunction | | p-Value |
|---|---|---|---|---|---|
| N, total | 139 | | 167 | | |
| Age [median] | 66.0 | | 66.0 | | |
| NT-proBNP [pgml] median | 397.2 | | 555.5 | | 0.048* |
|  | N | % | N | % | |
| NYHA I | 97 | 69.8% | 109 | 65.3% | >=0.05 |
| NYHA II | 30 | 21.6% | 38 | 22.8% | >=0.05 |
| NYHA III | 12 | 8.6% | 19 | 11.4% | >=0.05 |
| NYHA IV | 0 | 0 | 1 | 0.6% | >=0.05 |
| LVEF <30% | 6 | 4.3% | 8 | 4.8% | >=0.05 |
| LVEF 30-50% | 24 | 17.3% | 37 | 22.2% | >=0.05 |
| LVEF >50% | 109 | 78.4% | 122 | 73.1% | >=0.05 |
| Arterial Hypertension | 83 | 59.7% | 96 | 57.5% | >=0.05 |
| Blood pressure, systolic | 54 | 38.8% | 53 | 31.7% | >=0.05 |
| Blood pressure, diastolic | 24 | 17.3% | 23 | 13.8% | >=0.05 |
| Dyspnea | 53 | 38.1% | 76 | 45.5% | >=0.05 |
| Edema | 13 | 9.4% | 18 | 10.8% | >=0.05 |
| Angina Pectoris | 37 | 26.6% | 41 | 24.6% | >=0.05 |
| AMI Anamnese | 22 | 15.8% | 29 | 17.4% | >=0.05 |
| Arrhytmia | 6 | 4.3% | 12 | 7.2% | >=0.05 |

The present data suggest that when compared to data obtained in blood donors (Example 3) the majority of patients presenting to cardiologists has elevated NT-proBNP levels. NT-proBNP levels increased with levels of symptoms and with impairment of left ventricular ejection fraction. The fact that elevated NT-proBNP levels were recorded in asymptomatic individuals and in individuals with unimpaired ejection fraction indicates that NT-proBNP recognizes cardiac complication earlier than current gold standard methodology used by cardiologists. In the present study it was found that kidney function was frequently impaired based on creatinin levels in a group of patients with evidence of cardiac complication. This is in contrast to a study in blood donors where significantly lower and normal creatinin levels were found in a population of similar age (see Example 3). The study suggests that both components, kidney function and cardiac complication, need to be considered, and the data also indicate that mild to moderate renal dysfunction does not influence the interpretation of NT-proBNP values in the diagnosis and assessment of cardiac complication.

The data also indicate that thyroid dysfunction might be associated with cardiac dysfunction and might contribute to elevated NT-proBNP levels.

Example 6

Treatment options for a 46-year-old tumor patient with concurrent anaemia are being discussed. Treatment with anthracyclines appears to be a preferable option. To diagnose the risk of cardiovascular complication, the patient's NT-proBNP values are determined. The NT-proBNP-value of 800 pg/ml indicates an increased risk of cardiovascular complication, whereas the echocardiogram is not changed. Treatment with anthracyclines is commenced and the NT-proBNP-value is monitored at short intervals. Whereas echocardiogram and ultrasound examination are unchanged, the NT-proBNP-values are increasing to a value of 3500 pg/ml. Based on these values, a highly increased risk of suffering from a cardiovascular complication is diagnosed. The physicians discuss whether to interrupt treatment, to increase the haemoglobin-value, or to initiate cardiac therapy.

Example 7

A 62-year-old patient with depression with NT-proBNP value of 1200 pg/ml at presentation is being treated with tricyclic anti-depressants. Because of suspected cardiac dysfunction the patient is followed regularly with ECG, echocardiogram and NT-proBNP, NT-proBNP values significantly increase to 2050 pg/ml when measured at bi-weekly intervals. At the same time ECG and echocardiogram remain unchanged. The patient receives more intense treatment for cardiac dysfunction including loop diuretics. Thereafter NT-proBNP values decrease and alternate anti-depressant therapy is considered.

Example 8

48 patients suffering from chronic hepatitis C (predominantly genotype 1) were treated with 5 million units of non-pegylated interferon alpha 2b, three times a week, for 48 weeks. Additionally, the patients received ribavirin. Samples were taken and NT-proBNP levels were measured before treatment was initiated, at 24 weeks, at 48 weeks, and at 96 weeks. The measured NT-proBNP levels of all patients increased during treatment (median: 37.1, 44.3, 52.4, and 49 pg/ml NT-proBNP at the mentioned time points). However, one patient who already showed an increased level of NT-proBNP before initiation of treatment (368 pg/ml NT-proBNP) subsequently developed a clinically apparent cardiac insufficiency. This patient also showed a stronger increase of NT-proBNP during treatment than the other patients (the measured levels were: 368, 696, 376, and 413 pg/ml of NT-proBNP). In comparison, the highest levels of NT-proBNP measured in any of the other 47 patients were approximately 200, 370, 280, 430 pg/ml at the mentioned time points. The second to the highest level measured in the other patients at 96 weeks (430 pg/ml) was approximately 280 pg/ml of NT-proBNP. Thus, the present invention would have allowed to diagnose a risk of suffering from a cardiovascular complication in the patient who showed the level of 368 pg/ml of NT-proBNP before initiation of treatment.

Example 9

98 patients suffering from breast cancer are treated with anthracycline. One patient shows an increased level of NT-proBNP already before treatment is initiated. During treatment the measured level of NT-proBNP of the patient increases strongly. The patient develops cardiac insufficiency. The increase of the NT-proBNP level is present before clinical symptoms of cardiac insufficiency have become apparent.

What is claimed is:

1. A method for diagnosing a risk of a patient of a specific gender of suffering from a cardiovascular complication as a consequence of cardiotoxic medication, wherein said diagnosing is carried out before treatment with said cardiotoxic medication and said patient has no clinical history of cardiovascular complication, said method comprising the steps of:
   measuring a concentration of NT-proBNP in a body fluid sample from said patient, and
   diagnosing the risk of the patient by comparing the measured concentration to known concentrations associated with a risk in a patient of a specific gender,
   wherein the specific gender is male, the body fluid sample is plasma, and a plasma concentration of more than 60 and less than 1000 pg/ml of NT-proBNP is associated with an increased risk of suffering from a cardiovascular complication.

2. A method for diagnosing a risk of a patient of a specific gender of suffering from a cardiovascular complication as a consequence of cardiotoxic medication, wherein said diagnosing is carried out before treatment with said cardiotoxic medication and said patient has no clinical history of cardiovascular complication, said method comprising the steps of:
   measuring a concentration of NT-proBNP in a body fluid sample from said patient, and
   diagnosing the risk of the patient by comparing the measured concentration to known concentrations associated with a risk in a patient of a specific gender,
   wherein the specific gender is female, the body fluid sample is plasma, and a plasma concentration of more than 120 and less than 1000 pg/ml of NT-proBNP is associated with an increased risk of suffering from a cardiovascular complication.

3. A method for diagnosing a risk of a patient of a specific gender of suffering from a cardiovascular complication as a consequence of cardiotoxic medication, wherein said diagnosing is carried out before treatment with said cardiotoxic medication and said patient has no clinical history of cardiovascular complication, said method comprising the steps of:
   measuring a concentration of NT-proBNP in a body fluid sample from said patient, and
   diagnosing the risk of the patient by comparing the measured concentration to known concentrations associated with a risk in a patient of a specific gender,
   wherein the specific gender is male or female, the body fluid sample is plasma, and a plasma concentration of from 1000 to 5000 pg/ml of NT-proBNP is associated with a highly increased risk of suffering from a cardiovascular complication.

4. A method for diagnosing a risk of a patient of a specific gender of suffering from a cardiovascular complication as a consequence of cardiotoxic medication, wherein said diagnosing is carried out before treatment with said cardiotoxic medication and said patient has no clinical history of cardiovascular complication, said method comprising the steps of:
   measuring a concentration of NT-proBNP in a body fluid sample from said patient, and
   diagnosing the risk of the patient by comparing the measured concentration to known concentrations associated with a risk in a patient of a specific gender,
   wherein the specific gender is male or female, the body fluid sample is plasma, and a plasma concentration of more than 5000 pg/ml of NT-proBNP is associated with a very highly increased risk of suffering from a cardiovascular complication.

5. The method according to claim 1, 2, 3, or 4 wherein the cardiotoxic medication is selected from the group consisting of antineoplastics, tricyclic antidepressants, multiple sclerosis drugs, local anesthetics, interferon alpha, cocaine, androgens, anabolics, and HIV-antiviral drugs.

6. The method according to claim 5 wherein the cardiotoxic medication is an antineoplastic.

7. The method according to claim 5 wherein the cardiotoxic medication comprises an antineoplastic medication comprising an anthracycline.

8. The method according to claim 5 wherein the cardiovascular complication is selected from the group consisting of coronary heart disease, acute coronary syndrome, myocardial infarction, left ventricular dysfunction, and congestive heart failure.

9. The method according to claim 1, 2, 3, or 4 wherein the concentration of NT-proBNP is measured using one selected from the group consisting of a specifically binding ligand, an array, a microfluidic device, a chemiluminescence analyzer, and a robotic device.

10. The method according to claim 9 wherein the specifically binding ligand is an antibody or an aptamer.

11. The method according to claim 10 wherein the specifically binding ligand is labeled.

\* \* \* \* \*